United States Patent
Ikeda et al.

(10) Patent No.: US 9,606,066 B2
(45) Date of Patent: Mar. 28, 2017

(54) ANALYZER AND ANALYSIS METHOD

(75) Inventors: Yuji Ikeda, Kobe (JP); Ryoji Tsuruoka, Kobe (JP)

(73) Assignee: IMAGINEERING, INC., Kobe (JP)

( * ) Notice: Subject to any disclaimer, the term of this patent is extended or adjusted under 35 U.S.C. 154(b) by 83 days.

(21) Appl. No.: 14/206,289

(22) PCT Filed: Sep. 10, 2012

(86) PCT No.: PCT/JP2012/073068
§ 371 (c)(1),
(2), (4) Date: Nov. 19, 2014

(87) PCT Pub. No.: WO2013/039036
PCT Pub. Date: Mar. 21, 2013

(65) Prior Publication Data
US 2015/0085281 A1 Mar. 26, 2015

(30) Foreign Application Priority Data
Sep. 12, 2011 (JP) .................................. 2011-198903

(51) Int. Cl.
*G01J 3/30* (2006.01)
*G01N 21/71* (2006.01)
*G01J 3/443* (2006.01)

(52) U.S. Cl.
CPC ............ *G01N 21/718* (2013.01); *G01J 3/443* (2013.01); *G01N 2201/06113* (2013.01); *G01N 2201/08* (2013.01); *G01N 2201/125* (2013.01)

(58) Field of Classification Search
CPC ........ G01N 21/718; G01N 21/67; G01N 1/28; H03B 5/32
See application file for complete search history.

(56) References Cited

U.S. PATENT DOCUMENTS

2007/0069829 A1* 3/2007 Gehring .................. H03B 5/06
331/158

FOREIGN PATENT DOCUMENTS

JP      2001-159610 A      6/2001
JP      2001159610 A  *   6/2001 ............... G01N 1/28
(Continued)

OTHER PUBLICATIONS

"Microwave-Enhanced Laser-Induced Breakdown Spectroscopy", 14th Int. Symp. on Appl. Laser Techniques to Fluid Mechanics, Lisbon, Portugal, Jul. 7-10, 2008 by Masashi Kaneko.*

(Continued)

*Primary Examiner* — Tarifur Chowdhury
*Assistant Examiner* — Jamil Ahmed
(74) *Attorney, Agent, or Firm* — Bacon & Thomas, PLLC

(57) ABSTRACT

The objective of the present invention is to reduce the dispersion of a powdered substance, which is the target substance, during the analysis period in an analyzing device that analyzes the target substance by analyzing the light originated from the substance which is in the plasma state. The present invention relates to an analyzing device including a plasma generation means which generates plasma in the space and maintains plasma using the energy of EM radiation emitted from a radiation antenna; and an optical analysis means which analyzes a target substance by analyzing the plasma light generated from target substance of plasma state in the plasma area during the plasma maintenance period where the plasma is maintained by the plasma generation means using the energy of EM radiation. The plasma generation means emits the EM radiation from the radiation antenna in continuous waves during the plasma maintenance period.

13 Claims, 4 Drawing Sheets

(56) References Cited

FOREIGN PATENT DOCUMENTS

| JP | 2010-25869 A | 2/2010 | |
|---|---|---|---|
| JP | 2010025869 A * | 2/2010 | ............. G01N 21/67 |
| WO | 2012/036138 A1 | 3/2012 | |

OTHER PUBLICATIONS

Search Report issued in corresponding PCT application No. PCT/JP12/073068, 2012.
Kaneko et al. "Microwave Assisted Induced Breakdown Spectroscopy", Research of 89-20095366, 2009.

* cited by examiner

Fig. 2
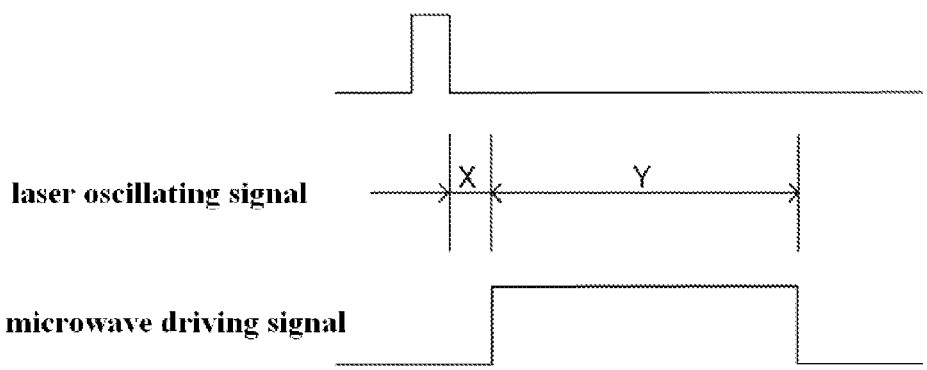
[Fig. 3]
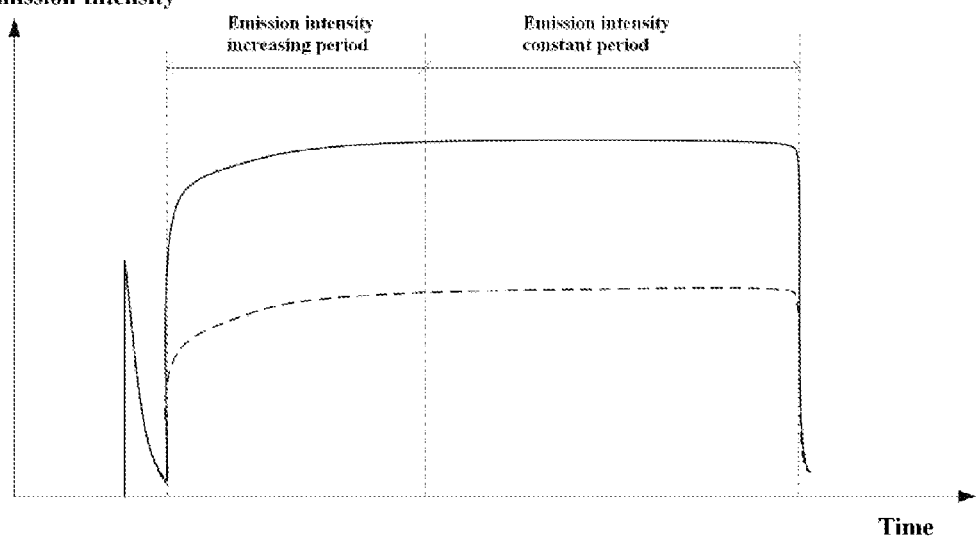

ANALYZER AND ANALYSIS METHOD

TECHNICAL FIELD

The present invention relates to analyzing device and analyzing method for analyzing a target substance by analyzing the light that is emitted from plasma.

BACKGROUND

Analyzing devices or analyzing methods for analyzing target substance by analyzing the light that is emitted from plasma are known. For example, JP2009-70586A1 discloses this kind of analyzing device.

Specifically, JP2009-70586A1 describes a measurement device using Laser-Induced Breakdown Spectroscopy. This measurement device has plasma generation device that generates plasma using energy of microwaves triggered by electron generated by laser induced breakdown. In the plasma generation device, microwave pulses are oscillated from microwave generator and microwave pulses are emitted from antenna. In the plasma generation area where plasma is generated by the laser light, plasma thus absorbs the microwave energy and then the plasma expands.

PRIOR ART DOCUMENT

Patent Document

[Patent Document 1] JP2009-70586A1

SUMMARY OF INVENTION

Problems to be Solved

In a conventional analyzing device, microwave pulses are emitted repetitively to plasma area, where a target substance exists, from the radiation antenna. In the plasma area, the microwave energy is applied in the pulsed condition, and shockwaves occur by the microwave pulses. Therefore, it was difficult to analyze accurately the powdered substance because the substance is destroyed by the shockwaves.

Present invention is in view of this respect, and the objective of the present invention is to reduce the dispersion of powdered substance, which is a target substance, during the analysis period in an analyzing device that analyzes the target substance by analyzing the light originated from the substance that is in the plasma state.

Means for Solving the Problems

The first invention relates to an analyzing device comprising: a plasma generation means which generates plasma in the space and maintains plasma using the energy of electromagnetic (EM) radiation emitted from a radiation antenna; and an optical analysis means which analyzes a target substance by analyzing the plasma light generated from the target substance that is in the plasma state in the plasma area during the plasma maintenance period where the plasma is maintained by the plasma generation means using the energy of EM radiation. The plasma generation means emits the EM radiation from the radiation antenna in continuous waves during the plasma maintenance period.

In the first invention, the plasma generation means radiates the EM radiation in continuous wave (CW) during a plasma maintenance period where the plasma is maintained by the energy of the EM radiation. In the plasma area where the target substance is existing, the energy of EM radiation is provided stable without pulsing like in EM radiation pulse. Therefore, the occurrence of shockwave due to EM radiation in the plasma area can be reduced during the plasma maintenance period.

In the second invention, the target substance of the first invention is moved to the plasma area during the plasma maintenance period.

The third invention relates to first or second invention wherein the plasma generation means generates EM radiation from the radiation antenna when pulse signals of constant voltage is received. The optical analysis means analyzes the target substance based on the emission intensity of plasma light during an analyzing period. The analysis period is set within a constant emission intensity period where the variation of the emission intensity of the plasma light is less than or equal to a predetermined value.

The fourth invention relates to one of first to third inventions, wherein the target substance is a powdered material and the output of the EM radiation during the plasma maintenance period is set to the value so that the target substance does not disperse.

The fifth invention relates to the fourth invention, wherein in the plasma generation means, the output of the EM radiation during the plasma maintenance period is set so that the maximum luminous intensity of the plasma light in the maintenance period is larger compared to the period prior to the emission of EM radiation.

The sixth invention relates to one of first to fifth inventions, wherein the optical analysis means analyzes the plasma light during the plasma maintenance period, and calculates the mixture ratio of the element included in the target substance.

The seventh invention relates to one of first to sixth inventions, wherein the plasma generation means maintains the plasma generated by the laser light outputted from a microchip laser using the energy of EM radiation.

The eighth invention relates to one of first to sixth inventions, wherein the plasma generation means maintains the plasma generated by the spark discharge using the energy of EM radiation.

The ninth invention relates to an analyzing method comprising: a plasma generation step which generates plasma in the space and maintains plasma using the energy of EM radiation emitted from a radiation antenna; and an optical analysis step which analyzes a target substance by analyzing the plasma light generated from target substance of plasma state in the plasma area during the plasma maintenance period where the plasma is maintained in the plasma generation step using the energy of EM radiation. The EM radiation is emitted from the radiation antenna in continuous waves during the plasma maintenance period.

The tenth invention relates to ninth invention wherein the target substance is moved to the plasma area during the plasma maintenance period.

Advantage of the Present Invention

In the present invention, the occurrence of shockwave originated from EM radiation is inhibited because the energy of the EM radiation is provided stably to the plasma area. The analysis period, in which the optical analysis means analyzes, resides in the plasma maintenance period. This allows inhibiting the disperse of the target substance, which is a powdered material, in the plasma area during the

BRIEF DESCRIPTION OF THE DRAWINGS

FIG. 2 is a time chart showing a time relationship between a pulse oscillation signal and an EM wave driving signal.

FIG. 3 is a graph showing a change of a luminous intensity of the light originated from the plasma generated by a plasma generation device of the first embodiment.

DESCRIPTION OF THE PREFERRED EMBODIMENTS

The embodiments of the present invention are detailed with reference to the accompanying drawings. The embodiments below are the preferred embodiments of the invention, but are not intended to limit the scope of present invention and application or usage thereof.

First Embodiment

Figure 1:
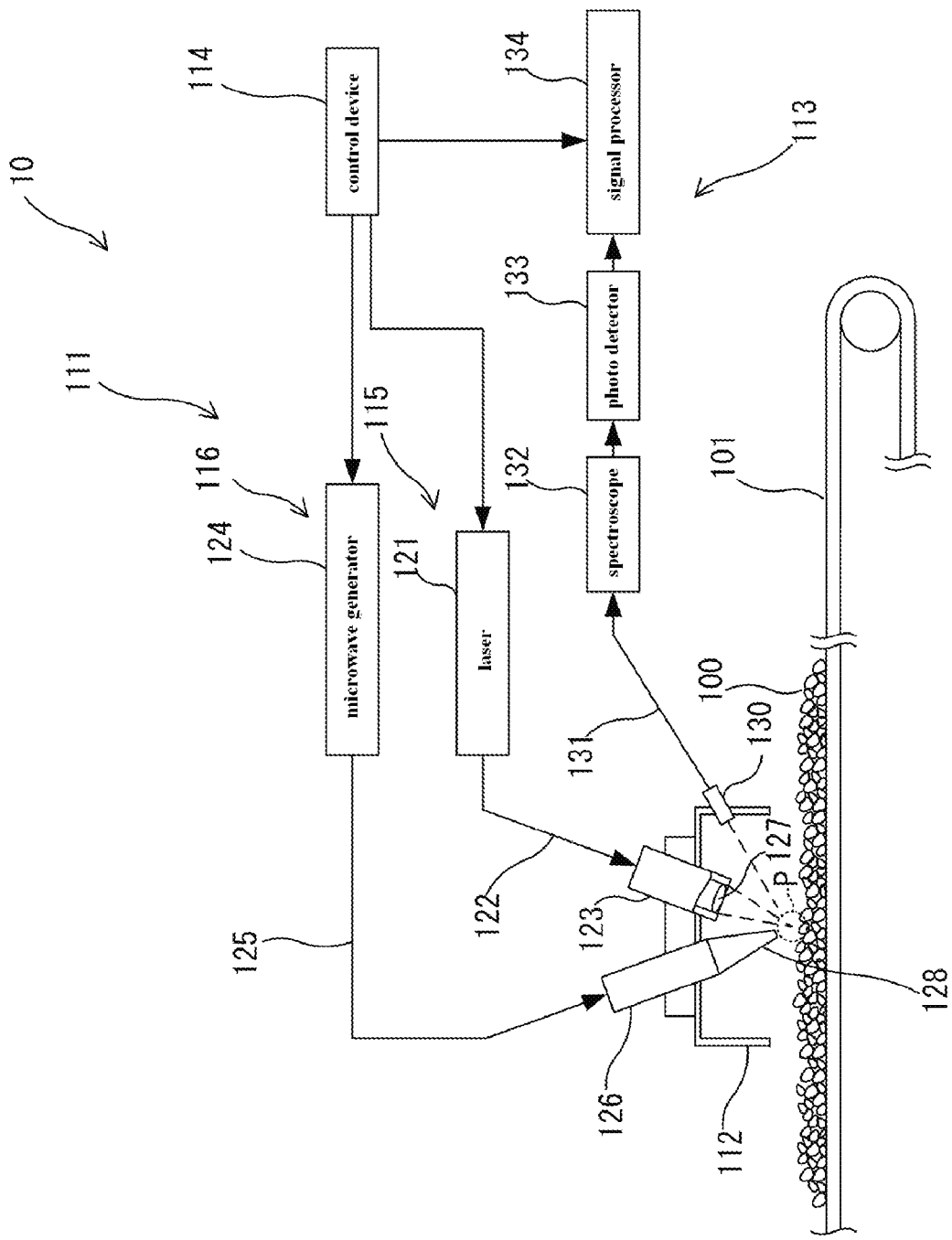
FIG. 1 illustrates a structure of an analyzing device according to the first embodiment.

Analyzing device 10 of first embodiment is a device which analyze the component of target substance 100. Here, target substance 100 is a powdered material. Analyzing device 10 is used for detecting impurities, for example. As shown in FIG. 1, analyzing device 10 is installed on belt conveyer 101 that moves target substance 100. Analyzing device 10 has plasma generation device 111, cavity 112, optical analyzing device 113, and controller 114.

Cavity 112 is a container having a microwave resonant structure. Cavity 112 is formed semi-cylindrical in which the lower side is opened. Cavity 112 is made of meshed material. Size of the mesh is designed so that the microwave that is emitted from radiation antenna 112 (which will be described later) to an internal space of cavity 112 does not leak outside. Laser probe 123 and antenna probe are installed in the upper face of cavity 112. Controller 114 controls plasma generation device 111 and optical analyzing device 113.

Structure of Plasma Generation Device

Plasma generation device 111 is one of the plasma generation means that generates plasma in the space, and maintains plasma using the energy of the microwaves emitted from radiation antenna 128. Plasma generation device 111 feeds energy momentarily to a material in the space to make this material into plasma state, i.e., initial plasma. Microwaves are irradiated for a predetermined period to the initial plasma to maintain the plasma state.

As shown in FIG. 1, plasma generation device 111 has laser oscillation device 115 and EM wave emitting device 116. Laser oscillation device 115 has laser light source 121, optical fiber 122, and laser probe 123. EM wave emitting device 116 has microwave oscillator 124, microwave transmission line 125, and antenna probe 126.

Laser light source 121 oscillates laser light for generating initial plasma when laser oscillation signal is received from controller 114. Laser light source 121 is connected to laser probe 123 through optical fiber 122. Light collecting optics 127 for collecting the laser light that has passed optical fiber 122 is installed in the front edge of laser probe 123. Laser probe 123 is attached in cavity 112 so that its front edge faces the internal space of cavity 112. The focal point of light collecting optics 127 is positioned at a position little lower than the lower side opening of cavity 112. Laser light oscillated from laser light source 121 passes light collecting optics 127 of laser probe 123 and is focused at the focal point of light collecting optics 127.

Here, laser light source 21 is a microchip laser and light collecting optics 127 is a convex lens, for example.

In laser oscillation device 115, the output of laser light source 121 is set so that the energy density of the laser light, which is focused at the focal point of light collecting optics 127, becomes breakdown threshold of target substance 100 or more at the focal point. That is, the output of laser light source 121 is set larger than or equal to the value necessary for target substance 100 turning to plasma state.

Microwave oscillator 124 continuously outputs the microwaves during the pulse width time of the EM wave driving signal when the microwave driving signal is received from controller 114. The EM wave driving signal is a pulse signal with a constant voltage. The output of the microwaves from microwave oscillator 124 is 100 watts or less, e.g. 80 watts, so that the powdered target substance 100 does not disperse. Microwave oscillator 124 is connected to antenna probe 126 through microwave transmission line 125. Antenna probe 126 has radiation antenna 128 installed thereon for emitting the microwaves that has passed microwave transmission line 125. Antenna probe 126 is attached so that the front end of the radiation antenna 128 faces toward the focal point of light collecting optics 127. Radiation antenna 128 is installed so that the focal point of light collecting optics 127 is covered by the strong electric field area produced by the microwaves.

Microwave oscillator 124 outputs the microwaves of 2.45 GHz. In microwave oscillator 124, the semiconductor oscillator generates microwaves. An oscillating semiconductor oscillator that oscillates microwaves of other bandwidth may be used instead.

Structure of Light Analyzing Device

Optical analyzing device 113 constitutes the optical analysis means that analyze the plasma light originated from target substance 100. Target substance is in plasma state and is located in plasma area P during the plasma maintenance period where plasma generation device 111 maintains plasma by microwave energy. Optical analyzing device 113 thus analyze target substance 100. Optical analyzing device 113 analyzes target substance 100 using time integral of luminous intensity of plasma light during the analysis period (which will be described later) within the plasma maintenance period. Optical analyzing device 113 has optical probe 130, optical fiber 131, spectroscope 132, photo-detector 133, and signal processor 134.

Optical probe 130 is a device for deriving the plasma light of an internal space of cavity 112. In optical probe 130, lens that captures the light of large range is attached to the front edge of a cylindrical casing. Optical probe 130 is attached to the side surface of cavity 112 so that the plasma light originated from the entire area of plasma area P reaches the lens, Spectroscope 132 is connected to optical probe 130 through optical fiber 131. The plasma light that entered optical probe 130 is captured by spectroscope 132. Spectroscope 132 distributes the incident plasma light to the different direction depending on wavelength using diffraction grating or prism.

The shutter for dividing the analysis period for analyzing plasma light is installed at an entrance of spectroscopic 132. The shutter is switched by controller 114 between open state that allows light entering spectroscope 132 and closed state that prohibits light from entering spectroscope 132. If the exposure timing of photo-detector 133 is controllable, the analysis period can be divided by controlling photo-detector 133.

Photo-detector 133 is installed so that the light dispersed by spectroscope 132 of predetermined wavelength band can be received. Photo-detector 133 photoelectric converts the received wavelength band light to an electric signal and then outputs the electric signal. Charge coupled device can be used for photo-detector 133. The electric signal outputted from photo-detector 133 is input to signal processor 134.

Signal processor 134 calculates the time integral of luminous intensity for each wavelength based on the electric signal outputted from photo-detector 133. Signal processor 134 calculates the time integral of luminous intensity for each wavelength, i.e. luminescence spectrum of the plasma light that entered spectroscope 132 during the analysis period where the shutter is in open state. Signal processor 134 detects the wavelength component having a strong luminous intensity based on the time integral of luminous intensity for each wavelength, and identifies the material corresponding to the detected wavelength as a component of target substance 100.

Operation of Analyzing Device—

The analysis operation where analyzing device 10 analyzes the component of target substance 100 will be described. The analysis operation is done while belt conveyer 101 is operating. In the analysis operation, the plasma generation and maintenance operation by plasma generation device 111 is done in conjugation with the optical analysis operation by optical analyzing device 113.

First, plasma generation maintenance operation will be described. In the plasma generation maintenance operation, plasma generation device 111 generates and maintains the plasma. Plasma generation device 111 drives laser light source 121 based on an instruction of controller 114 and generates plasma, then drives microwave oscillator 124 to irradiate microwaves to initial plasma for maintaining plasma state.

Controller 114 outputs laser oscillation signal (a short pulse signal) to laser light source 121. Laser light source 121 oscillates single pulse of pulsed laser light when laser oscillation signal is received. The laser light that is oscillated from laser light source 121 is focused to the surface of target substance 100 by light collecting optics 127. High density energy is fed to target substance 100 momentarily.

At the surface of target substance 100, the energy density increases at laser irradiation area and when the energy density exceeds the breakdown threshold of target substance 100, the material in the laser irradiation area ionizes and becomes plasma state. Thus, initial plasma which is made from target substance 100, i.e. is generated.

Controller 114 outputs microwave driving signal to microwave oscillator 124 following the falling edge of laser oscillation signal as shown in FIG. 2. Microwave oscillator 124 outputs continuous wave (CW) of the microwaves to radiation antenna 128 when the microwave driving signal is received. The microwaves are emitted from radiation antenna 128 to the internal space of cavity 112. The microwaves are emitted from radiation antenna 128 during the pulse width period of the microwave driving signal. The time X from falling edge of the laser oscillation signal to the rising edge of EM wave driving signal is set so that the emission of the microwaves can begin before the initial plasma disappears.

In the internal space of cavity 112, strong electric field (area where electric field is relatively strong in the internal space of cavity 112) is formed centering the focal point of light collecting optics 127. Initial plasma enlarges by absorbing the microwave energy and becomes ball-like microwave plasma. The plasma area P, where the microwave plasma exists, is formed so that the surface of target substance 100 is included. The microwave plasma is maintained during microwave emission period Y. Here, microwave emission period Y will be equal to plasma maintenance period.

When microwave oscillator 124 terminates the output of microwaves at the fall edge of the EM wave driving signal, microwave plasma disappears. Microwave radiation period Y is, for example, few tens micro second to few tens second. The output value of the microwaves are set to a predetermined value, e.g. 80 watts, in microwave oscillator 124. The microwave plasma is thereby prevented from turning to heat plasma even when the microwaves are outputted for a long time.

The change of luminous intensity of the plasma light originated from the plasma in the period between the generation of the initial plasma and the disappearance of microwave plasma will be described. As shown in FIG. 3, the peak luminous intensity of initial plasma can be seen momentary, and then the luminous intensity decreases to a minimum value which is close to zero. When the luminous intensity becomes the minimum, the microwave luminous intensity increases (luminous intensity increasing period), and following this period, the microwave luminous intensity becomes constant (luminous intensity constant period). In this period, change or increase of luminous intensity of plasma is less than or equal to predetermined value.

In plasma generation device 111 of the first embodiment, the output of the microwave at the plasma maintenance period is set so that the maximum luminous intensity of the plasma light during the plasma maintenance period becomes larger compared to that of ante-emission period of the microwaves as shown in the solid line of FIG. 3. This prevents dispersion of target substance 100, and enables accurate analysis of target substance 100 because a large luminous intensity can be obtained from the plasma light. However, when a sufficient luminous intensity can be obtained, the output of the microwaves during the plasma maintenance period can be set so that the you may set the output of the microwave at the plasma maintenance period so that the maximum luminous intensity of the plasma light becomes larger in the ante-emission period compared to that of the plasma maintenance period as shown in broken line of FIG. 3.

In the optical analysis operation, optical analyzing device 113 analyzes the light (plasma light) originated from target substance 100 which is in the plasma state. Optical analyzing device 113 analysis the component of target substance 100 through spectrum analysis of the plasma light. In optical analyzing device 113, analysis period is set within the luminous intensity constant period (mentioned above) in the plasma maintenance period. The target substance is thereby analyzed based on the luminous intensity of the plasma light. Controller 114 controls the shutter of the spectroscope so that the entire period of the luminous intensity stable period is set to the analyzing period. Simultaneously, photoelectric conversion period for photo-detector 133 is set. Instead, part of the luminous intensity stable period can be set to the analysis period.

During the generation of initial plasma, target substance 100 disperses by the shockwave of the laser light. However, the position where target substance 100 dispersed has passed over plasma area P at the beginning of the luminous intensity constant period because belt conveyer 101 is moving. Target substance 100 that exists in plasma area P at the beginning the luminous intensity constant period is in plasma area P during the plasma maintenance period. Target substance 100 that has entered plasma area P in the plasma maintenance period is not affected by dispersion, and the movement of the material is very small.

In optical analyzing device 113, plasma light emitted from target substance 100 that is in the plasma and positioned in the plasma area P enters spectroscope 132 via optical probe 130 and optical fiber 131 sequentially only during the luminous intensity constant period, i.e. analysis period as shown in FIG. 3.

Figure 4:
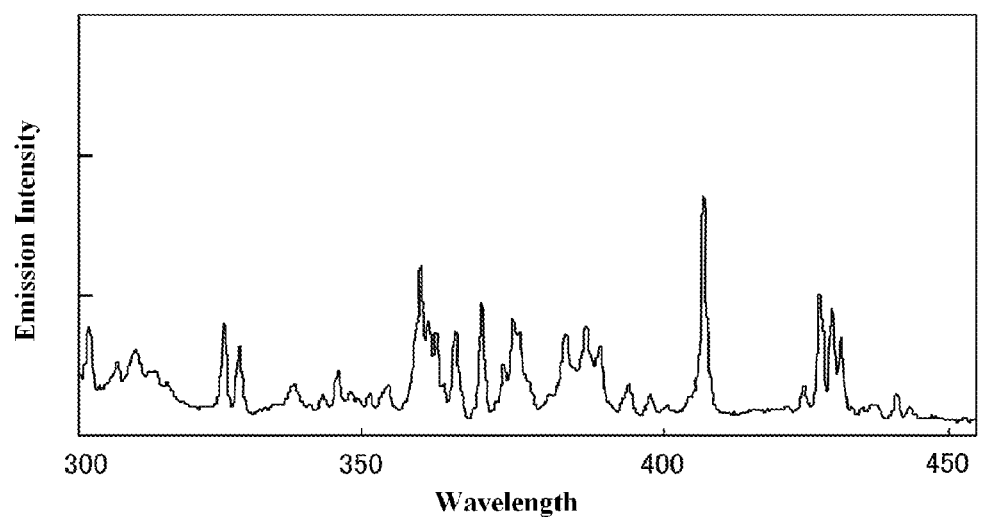
FIG. 4 is a spectrum chart showing an integrated value of luminous intensity for each wavelength of the light originated from the plasma generated by a plasma generation device of the first embodiment.

In spectroscope 132, the incident plasma light is dispersed to the different direction depending on its wavelength. Then, the plasma light of a predetermined wavelength band reaches photo-detector 133. In the photo-detector 133, detected plasma light is photoelectric converted to an electric signal for each wavelength band. In signal processor 134, the time integral value of the luminous intensity during the luminous intensity constant period (analyzing period) is calculated for each wavelength based on the output signal of photo-detector 133. Signal processor 134 creates a spectrum chart as shown in FIG. 4 that shows the time integral value of the luminous intensity for each wavelength. Signal processor 134 detects wavelength where the peak of the luminous intensity appears based on time integral value for each wavelength, and identifies the material (atom or molecule) that corresponds to the detected wavelength as the component of target substance 100.

For example, signal processor 134 identifies the component of target substance 100 as molybdenum when the peak of the luminous intensity appears at 379.4 mm. When the peak luminous intensity appears at 422.7 mm, calcium is identified as the component of target substance 100. When the peak luminous intensity appears at 345.2 mm, cobalt is identified as the component of target substance 100. When the peak luminous intensity appears at 357.6 mm, chrome is identified as the component of target substance 100.

Signal processor 134 may display the spectrum chart as shown in FIG. 4 on the monitor of analyzing device 10. The user of analyzing device 10 can identify the component included in the target substance by seeing this spectrum chart.

Advantage of the First Embodiment

In this embodiment, shockwave due to microwaves is inhibited because the microwave energy is fed stably to plasma area P during the plasma maintenance period. The analysis period where optical analyzing device 113 analyzes exists within the plasma maintenance period. Thus, dispersion of the target substance 100, i.e. powdered material, in plasma area P is reduced during the analysis period. This allows an analysis of target substance 100 in plasma area P in a state with small movement of material.

In the present embodiment, a powdered material can be analyzed untouched. Conventionally, target substance 100 (powdered material) was analyzed in a pellet state where the powdered material is hardened by binder. On the contrary, in the present embodiment, the noise originated from the binder does not appear in the luminous intensity because a powdered material can be analyzed in the original form. Thus, filter for eliminating noise is not necessary.

In the present embodiment, intensity of microwave plasma during the plasma maintenance period is not very large. Therefore, the metal forming radiation antenna 128 is not excited and can reduce the noise originating from the metal.

Modification 1

In this modification embodiment, signal processor 134 calculates the mixture ratio of multiple component included in target substance 100. The plasma maintained by plasma generation device 111 of the first embodiment is larger than the plasma which is generated using laser light only. Therefore, the calculation of the mixture ratio of the component becomes easier because large plasma light can be used for the calculation.

Signal processor 134 stores the standard curve data that shows the relation between the luminous intensity and the contained amount for each of the substances. Signal processor 134 detects two or more substances which corresponds to the peak wavelength of the luminous intensity, and calculates the contained amount of the detected substance based on the material based on the standard curve data. Signal processor 134 then calculates the ratio of the contents of the substance that corresponds to peak wavelength of the luminous intensity. Mixture ration of the components included in the target substance is thereby calculated.

This modification embodiment allows detecting whether the mixture ratio of a specific element of the medicine is in the predetermined range or not, when analyzing device 10 is used for the quality control of the medicine, for example. Signal processor 134 calculates the contained amount of components A and B in the medicine powder based on luminous intensity at their corresponding wavelength. Signal processor 134 then calculates the mixture ratio (weight ratio of the containing amount) of component B against component A based on containing amounts of components A and B.

Signal processor 134 may correct the containing amount of the substance that can be obtained from luminous intensity based on the energy of the reflected microwaves in radiation antenna 128 of EM wave emitting device 116. When the energy of the reflected microwaves is large, the luminous intensity becomes small. Because the energy of the microwaves necessary for maintaining the microwave plasma decreases. Signal processor 134 corrects the containing amount of the substance that is calculated from the luminous intensity when the energy of the reflected microwaves is large.

Second Embodiment

In the second embodiment. means for generating initial plasma is different from that of the first embodiment.

Figure 5:
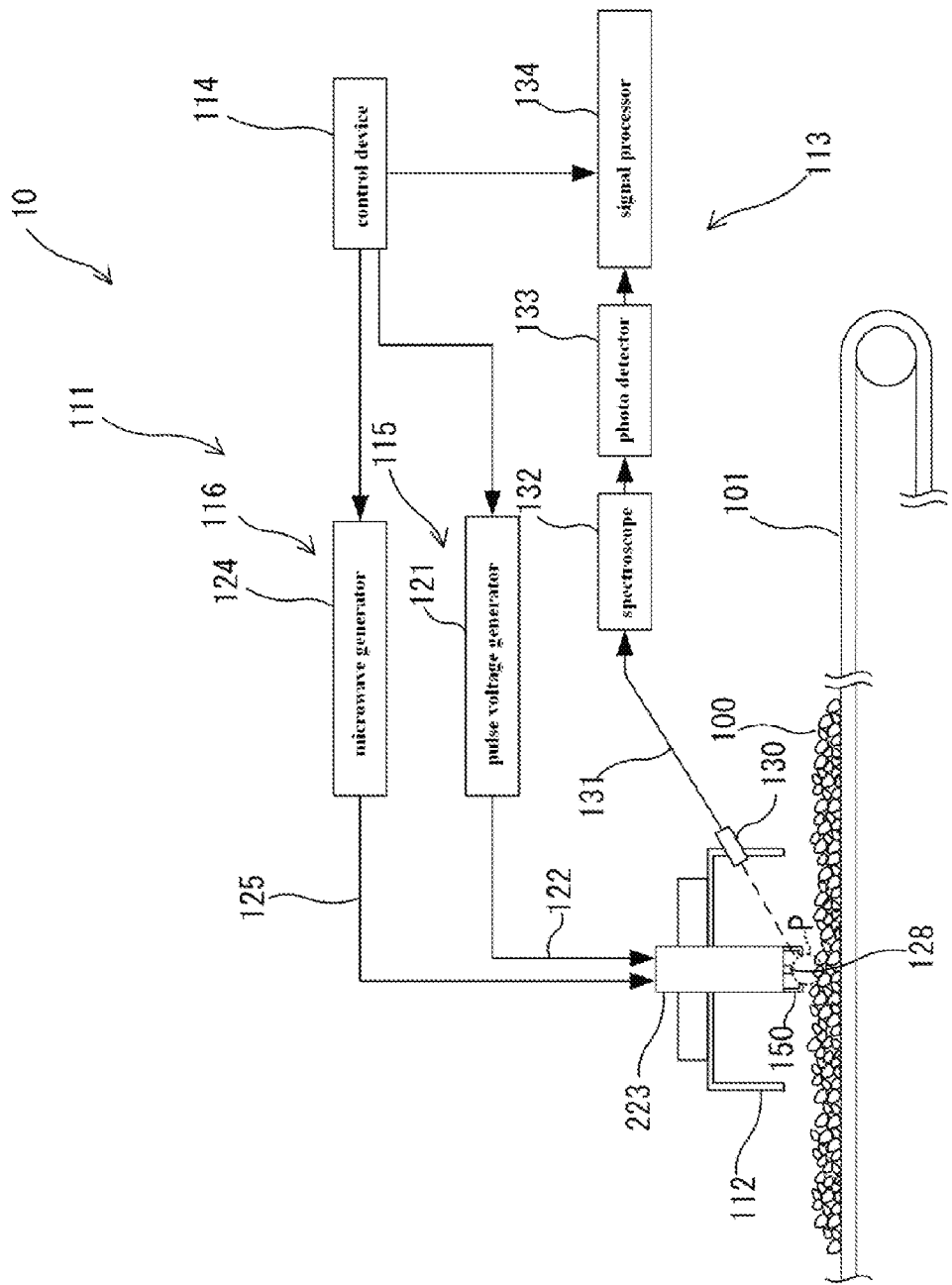
FIG. 5 illustrates a structure of an analyzing device according to the second embodiment.

In the second embodiment, spark plug 223 (electrical discharger) is used as for generating initial plasma as shown in FIG. 5. Controller 114 outputs a spark generation signal to pulse voltage generator 121 when initial plasma is generated. Pulse voltage generator 121 then outputs a high voltage pulse to spark plug 223, and a spark discharge is thereby generated in the discharge gap between electrodes 150 of spark plug 223. Initial plasma is generated in the spark discharge. The high voltage pulse is an impulse voltage signal having 6 to 40 kV peak voltage, for example.

In the second embodiment, radiation antenna 128 is buried inside spark plug 223. Controller 114 outputs a microwave driving signal to microwave oscillator 124 following the falling edge of the spark generation signal. Microwave oscillator 124 outputs the continuous microwave from radiation antenna 128 similarly to the first embodiment. The initial plasma that was generated by the spark discharge is then enlarged by absorbing the energy of the microwaves. Radiation antenna 128 may be installed separately with spark plug 223.

Other Embodiments

Following embodiments can be contemplated.

Analyzing device 10 may analyze target substance 100 that is other than powder material, e.g. metal piece.

Analyzing device 10 may have a moving mechanism that can move target substance 100 to plasma area P during the plasma maintenance period when there is no belt conveyer 101.

Laser light source 21 can be Nd:YAG laser light source, liquid laser light source, gas laser light source, semiconductor laser light source or a free electronic laser light source.

The initial plasma generation means is not only light source 121 or spark plug 223 but can be a thermal electron generator such as glow plug.

Besides detection of impurities or quality control of medicine, analyzing device 10 can be used for other purpose. For example, it can be used for calculating the containing amount of minerals included in food, detection of toxic, detection of impurities in metallic alloys or ceramics, or for safety management such as detection of radioactive substance. It can be used in the fields of environment optics, energy optics, aerospace engineering, geology, or life chemistry.

INDUSTRIAL APPLICABILITY

As discussed above, the present invention is useful for analyzing device and analyzing method that analyzes a target substance by analyzing light emitted from plasma.

EXPLANATION OF REFERENCE NUMERALS

10 Analyzing device
112 cavities
111 plasma generation device (plasma generation means)
113 light analyzing device (optical analysis means)
114 controllers
115 laser oscillation device
116 EM wave emitting devices
123 Laser probe
126 Antenna probe
130 Optical probe

The invention claimed is:

1. An analyzing device comprising:
a plasma generator which generates a plasma in a plasma area during a plasma generation period, and maintains the plasma in the plasma area during a plasma maintenance period using energy of electromagnetic (EM) radiation emitted from a radiation antenna, wherein the plasma generator emits the EM radiation from the radiation antenna in continuous waves during the plasma maintenance period;
an optical analyzer which analyzes a target substance by analyzing a plasma light generated from a plasma state of the target substance in the plasma area during a luminous intensity constant period of the plasma maintenance period;
wherein the target substance is a powdered material;
wherein during the plasma maintenance period, the plasma generator emits the EM radiation from the radiation antenna in continuous waves, and
wherein an output value of the EM radiation is set such that the plasma is prevented from turning to heat plasma, whereby the target substance does not disperse.

2. The analyzing device as claimed in claim 1, wherein the plasma generator generates EM radiation from the radiation antenna when pulse signals of constant voltage is received, and
the optical analyzer analyzes the target substance based on an emission intensity of plasma light during an analyzing period.

3. The analyzing device as claimed in claim 1, wherein during said luminous intensity constant period, variation of an emission intensity of the plasma light is less than or equal to a predetermined value.

4. The analyzing device as claimed in claim 1, wherein in the plasma generator, the output of the EM radiation during the plasma maintenance period is set so that the maximum luminous intensity of the plasma light is larger in the maintenance period compared to the period prior to the emission of EM radiation.

5. The analyzing device as claimed in claim 1, wherein the optical analyzer analyzes the plasma light during the plasma maintenance period, and calculates a mixture ratio of an element included in the target substance.

6. The analyzing device as claimed in claim 1, wherein the plasma generator generates the plasma by a laser light outputted from a microchip laser.

7. The analyzing device as claimed in claim 1, wherein the plasma generator generates the plasma by a spark discharge.

8. An analyzing method, comprising the steps of:
generating a plasma in a plasma area during a plasma generating period, and maintaining the plasma in the plasma area during a plasma maintaining period using energy of EM radiation emitted from a radiation antenna; and
analyzing a target substance by analyzing a plasma light generated from a plasma state of the target substance in the plasma area during the plasma maintenance period; and
displaying a spectrum chart according to the target substance analysis;
wherein the target substance is a powdered material;
wherein during the plasma maintenance period, the plasma generator emits the EM radiation from the radiation antenna in continuous waves, and
wherein an output value of the EM radiation is set such that the plasma is prevented from turning to heat plasma, whereby the target substance does not disperse.

9. The method of claim 8, wherein
the EM radiation is emitted from the radiation antenna in continuous waves during the plasma maintenance period.

10. The method of claim 8, wherein the plasma maintaining period includes a luminous intensity constant period.

11. The method of claim 10, wherein:
the target substance is moved such that a target substance in the plasma area during the plasma generation period is removed from the plasma area before the luminous intensity constant period, and a target substance in the plasma that exists in the plasma area at the beginning of the luminous intensity constant period remains in the plasma area during the plasma maintenance period.

12. The method of claim 8, wherein the target substance is moved to the plasma area during the plasma maintenance period.

13. The analyzing device as claimed in claim 1, further comprising:
   a target substance conveyor which moves the target substance such that a target substance in the plasma area during the plasma generation period is removed from the plasma area before the luminous intensity constant period, and a target substance in the plasma that exists in the plasma area at the beginning of the luminous intensity constant period remains in the plasma area during the plasma maintenance period.

* * * * *